US012778563B2

(12) United States Patent
Kim et al.

(10) Patent No.: US 12,778,563 B2
(45) Date of Patent: Nov. 3, 2026

(54) SAMPLE COLLECTING SWAB TOOL AND METHOD FOR DETECTION OF RESPIRATORY PATHOGEN

(71) Applicant: SEEGENE, INC., Seoul (KR)

(72) Inventors: Won Sik Kim, Gyeonggi-do (KR); Myung Jun Seo, Seoul (KR)

(73) Assignee: SEEGENE, INC., Seoul (KR)

( * ) Notice: Subject to any disclaimer, the term of this patent is extended or adjusted under 35 U.S.C. 154(b) by 265 days.

(21) Appl. No.: 18/697,069

(22) PCT Filed: Oct. 26, 2022

(86) PCT No.: PCT/KR2022/016432
§ 371 (c)(1),
(2) Date: Mar. 29, 2024

(87) PCT Pub. No.: WO2023/075394
PCT Pub. Date: May 4, 2023

(65) Prior Publication Data

US 2024/0398393 A1 Dec. 5, 2024

(30) Foreign Application Priority Data

Oct. 29, 2021 (KR) ........................ 10-2021-0147202

(51) Int. Cl.
*A61B 10/00* (2006.01)
*A61F 13/38* (2006.01)

(52) U.S. Cl.
CPC .......... *A61B 10/0051* (2013.01); *A61F 13/38* (2013.01); *A61B 2010/0003* (2013.01)

(58) Field of Classification Search
CPC ........ A61B 2010/0003; A61B 10/0045; A61B 10/0051
See application file for complete search history.

(56) References Cited

U.S. PATENT DOCUMENTS

| | | | | |
|---|---|---|---|---|
| 2012/0067144 A1* | 3/2012 | Slowey | A61B 10/0051 | 73/864.73 |
| 2013/0184684 A1* | 7/2013 | Yardley | A61F 13/126 | 606/162 |
| 2014/0083213 A1* | 3/2014 | Triva | A61B 10/02 | 73/864 |

(Continued)

FOREIGN PATENT DOCUMENTS

| | | |
|---|---|---|
| CN | 213030715 U | 4/2021 |
| DE | 20 2021 103298 U1 | 7/2021 |

(Continued)

OTHER PUBLICATIONS

Falsey A. R., Formica M. A. & Walsha E. E. 2012 Yield of sputum for viral detection by reverse transcriptase PCR in adults hospitalized with respiratory illness. J. Clin. Microbiol. 50, 21-24.

(Continued)

*Primary Examiner* — Eric F Winakur
(74) *Attorney, Agent, or Firm* — Harness, Dickey & Pierce, P.L.C.

(57) ABSTRACT

The present invention relates to a sample collecting swab tool and a method for detection of respiratory pathogens. The present invention relates to a swab tool in which two positions for gripping the swab tool, that is, two gripping points, are formed so as to make it easy to precisely control the force on the swab tool according to the sample collection site (e.g., nasal cavity or oral cavity), whereby swab samples can be collected from sample collection sites accurately and easily in an amount sufficient enough to detect respiratory pathogens. In addition, the swab tool of the present invention can be used not only for sampling by experts but also for self-sampling by non-experts, and respiratory pathogens can be detected from collected samples.

13 Claims, 5 Drawing Sheets

(56) References Cited

U.S. PATENT DOCUMENTS

| | | | | |
|---|---|---|---|---|
| 2016/0367227 | A1* | 12/2016 | Triva | A61B 10/0045 |
| 2019/0033175 | A1 | 1/2019 | Caragiuli et al. | |
| 2019/0261961 | A1 | 8/2019 | Esfandiari | |
| 2021/0290210 | A1* | 9/2021 | Decker | A61B 10/0045 |
| 2021/0321991 | A1* | 10/2021 | Elliott | A61B 10/0045 |
| 2021/0378643 | A1* | 12/2021 | Roswech | A61B 10/0051 |
| 2022/0133283 | A1* | 5/2022 | Sayani | A61B 10/0051 600/569 |
| 2023/0172762 | A1* | 6/2023 | Chiarin | A61B 10/0045 604/1 |
| 2023/0194389 | A1* | 6/2023 | Ji | A61B 10/0045 422/501 |

FOREIGN PATENT DOCUMENTS

| | | | |
|---|---|---|---|
| JP | 2014-083386 | A | 5/2014 |
| KR | 10-0604145 | B1 | 7/2006 |
| KR | 20-2011-0006452 | U | 6/2011 |
| KR | 101 350 115 | B1 | 1/2014 |
| KR | 102 211 288 | B1 | 2/2021 |

OTHER PUBLICATIONS

Branche A. R., Walsh E. E., Formica M. A. & Falsey A. R. 2014 Detection of respiratory viruses in sputum from adults by use of automated multiplex PCR. J. Clin. Microbiol. 52, 3590-3596.

Jeong J., Kim K., Jeong S., Park J., Lee S. & Seo Y. 2014 Comparison of sputum and nasopharyngeal swabs for detection of respiratory viruses. J. Med. Virol. 86, 2122-2127.

International Search Report from corresponding PCT Application No. PCT/KR2022/016432, dated Feb. 13, 2023.

Extended European Search Report from corresponding EP Application No. 22887590.2, dated Sep. 17, 2025.

* cited by examiner

The collection of a nasal swab specimen

The collection of an oral swab specimen

The collection of a nasal swab specimen

The collection of an oral swab specimen

SAMPLE COLLECTING SWAB TOOL AND METHOD FOR DETECTION OF RESPIRATORY PATHOGEN

CROSS-REFERENCE TO RELATED APPLICATIONS

This application is a national phase application of PCT Application No. PCT/KR2022/016432 filed on Oct. 26, 2022, which claims the benefit and priority to 10-2021-0147202 filed on Oct. 29, 2021. The entire disclosures of the applications identified in this paragraph are incorporated herein by references.

FIELD OF THE INVENTION

The present invention relates to a swab device for collecting a specimen and a method for detecting a respiratory pathogen.

DESCRIPTION OF THE RELATED ART

Respiratory diseases cause serious mortality rates in especially, children, the elderly, and immunocompromised people. It is very important to identify causative pathogens for infection control and appropriate patient care. Respiratory pathogen testing has developed rapidly with the development of molecular diagnostic technology, especially real-time PCR. Real-time PCR, compared with conventional methods, is very sensitive and prompt and can simultaneously detect various pathogens.

Various upper respiratory tract (URT) samples and lower respiratory tract samples have been used for respiratory pathogen testing by molecular diagnosis.

In general, nasopharyngeal swab specimens and oropharyngeal swab specimens are widely used as upper respiratory tract samples. Meanwhile, sputum and bronchoalveolar lavage (BAL) samples are used as lower respiratory tract samples (Falsey et al., 2012; Branche et al., 2014; Jeong et al., 2014).

In recent years, real-time PCR diagnostic kits are receiving much attention due to the SARS-CoV-2 pandemic. For the diagnosis of coronavirus, nasopharyngeal swab specimens and oropharyngeal swab specimens are used as upper respiratory tract samples, and sputum and bronchoalveolar lavage are used as lower respiratory tract samples. The nasopharyngeal and oropharyngeal swab samples are obtained by collecting secretions from the nasopharynx and oropharynx using cotton swabs and then stored in transport media. The sputum is collected and stored in a sterile vessel after the mouth is rinsed with saline.

However, lower respiratory tract samples are difficult to collect and may require pretreatment before nucleic acid extraction, and especially, sputum samples cannot be applied in the early stages of infection in which patients have substantially no cough symptoms or a dry cough. Sampling by nasopharyngeal and oropharyngeal swabs has its limitation in that sampling needs to be conducted by experts, and is risky due to its aerosol-generating sampling method.

FIG. 1 shows a conventional swab device for collecting a specimen having a different shape, structure, and/or length according to a specimen collection site. For example, a swab device for collecting the nasopharyngeal swab specimen has a thin thickness and a long length of a fiber layer of a head part and a supporting part adjacent to the head part in order to collect a specimen from the nasopharynx. Meanwhile, the swab device for collecting the oropharyngeal swab specimen has a length as long as that of the swab device for collecting the nasopharyngeal swab specimen in order to collect the specimen from the oropharynx, but the thickness of the fiber layer of the head part and the supporting part adjacent to the head part is thicker than that of the swab device for collecting the nasopharyngeal swab specimen. In addition, the swab device for collecting the nasal swab specimen may include a stopper limiting the length of insertion of the head part into the nasal cavity in order to collect the specimen in the nasal cavity, and the length of the swab device may be shortened in order to control a precise force.

The conventional swab device for collecting a specimen has the shape, structure, and/or length enabling specimens to be collected from only a specific specimen collection site. Therefore, in a case of a kit for collecting specimens from two specimen collection sites, a swab device for collecting a specimen suitable for a specific specimen collection site should be included. This is not only limited in performing self-sampling by ordinary persons as non-experts, but also has a problem in economic efficiency because a swab device having two different shapes, structures, and/or lengths should be included in forming one package of a kit for collecting a specimen.

Accordingly, the present inventors recognized the necessity of developing a technology capable of performing precise force control in a customized manner according to a specimen collection site using one swab device.

Throughout this application, various patents and publications are referenced and citations are provided in parentheses. The disclosure of these patents and publications in their entities are hereby incorporated by references into this application in order to more fully describe this invention and the state of the art to which this invention pertains.

SUMMARY OF THE INVENTION

The present inventors have made efforts to develop a swab device for collecting a specimen capable of effectively collecting nasal swab specimens and oral swab specimens while overcoming the problems of the conventional swab devices for collecting a specimen described above. As a result, the present inventors have found that, as a result of forming two positions capable of gripping in one swab device, i.e., two gripping points, precise force control of the swab device is easily performed according to a specimen collection site (for example, nasal cavity or oral cavity), so that a swab specimen can be accurately and easily collected at the specimen collection site, a specimen amount sufficient to detect respiratory pathogens can be collected, the swab device can be used for self-sampling by ordinary persons as non-experts as well as sampling by experts, and the respiratory pathogens can be detected from the collected specimens, and thus completed the present invention.

Accordingly, it is an object of the present invention to provide a swab device for collecting a specimen.

It is another object of the present invention to provide a kit for collecting a specimen to detect a respiratory pathogen.

It is still another object of the present invention to provide a kit for detecting a respiratory pathogen.

It is another object of the present invention to provide a method for collecting a specimen to detect a respiratory pathogen.

It is still another object of the present invention to provide a method for detecting a respiratory pathogen.

Other objects and advantages of the present invention will become apparent from the detailed description to follow taken in conjugation with the appended claims and drawings.

DETAILED DESCRIPTION OF THIS INVENTION

In an aspect of the present invention, there is provided a swab device for collecting a specimen, comprising:

(a) a head part having a fibrous layer formed to collect a specimen; and (b) a supporting part supporting the head part and having a break point formed on an outer surface; wherein the supporting part comprises a first gripping point and a second gripping point, and the first gripping point is located adjacent to the head part.

The present inventors have made efforts to develop a swab device for collecting a specimen capable of effectively collecting nasal swab specimens and oral swab specimens while overcoming the problems of the conventional swab devices for collecting a specimen described above. As a result, the present inventors have found that, as a result of forming two positions capable of gripping in one swab device, i.e., two gripping points, precise force control of the swab device is easily performed according to a specimen collection site (for example, nasal cavity or oral cavity), so that a swab specimen can be accurately and easily collected at the specimen collection site, a specimen amount sufficient to detect respiratory pathogens can be collected, the swab device can be used for self-sampling by ordinary persons as non-experts as well as sampling by experts, and the respiratory pathogens can be detected from the collected specimens.

The specimens collected using the swab device of the present invention are respiratory specimens, and specifically, the respiratory specimens are nasal specimens and/or oral specimens.

The nasal specimen refers to a biopsy obtained from the nasal wall in a space that is empty in the nose, and specifically, is a nostril specimen. The nostril specimen represents a specimen taken from the front part of the nose, specifically the nasal wall of about 2-3 cm from the naris.

The present invention is characterized by enabling self-sampling by ordinary persons as non-experts as well as sampling by experts.

According to an embodiment of the present invention, the swab device for collecting a specimen is a self-sampling device.

Hereinafter, the present invention will be described in detail through exemplary drawings. In adding reference numerals to elements in each drawing, it should be noted that the same elements will be designated by the same reference numerals, if possible, although they are shown in different drawings. Further, in the following description of the present invention, a detailed description of known functions and configurations incorporated herein will be omitted when it may make the subject matter of the present invention rather unclear.

FIGS. 2 to 4 show swab devices for collecting a specimen according to an embodiment of the present invention.

Referring to FIGS. 2 to 4, the swab device for collecting a specimen 100 of the present invention largely includes (a) a head part 10; and (b) a supporting part 11.

(a) The head part 10 is in direct contact with a sample collection site and has a fibrous layer formed so as to collect a specimen.

FIG. 5 shows a head part 10 having a fiber layer formed thereon according to an embodiment of the present invention.

The fibrous layer formed on the head part so as to collect a specimen may be formed by various methods known in the art, and for example, the fibrous layer may be formed on the head part by a flocking method. According to the flocking method, an adhesive may be coated on the surface of the head part and small fiber yarns are vertically deposited in an electrostatic field.

According to another embodiment of the present invention, the thickness of the fibrous layer formed on the head part is 0.2-3 mm. Specifically, the thickness of the fibrous layer is 0.2-3 mm, 0.2-2.8 mm, 0.2-2.5 mm, 0.2-2.2 mm, 0.2-1.8 mm, 0.2-1.5 mm, 0.2-1.2 mm, 0.2-0.8 mm, 0.4-3 mm, 0.4-2.8 mm, 0.4-2.5 mm, 0.4-2.2 mm, 0.4-1.8 mm, 0.4-1.5 mm, 0.4-1.2 mm, 0.4-0.8 mm, 0.6-3 mm, 0.6-2.8 mm, 0.6-2.5 mm, 0.6-2.2 mm, 0.6-1.8 mm, 0.6-1.5 mm, 0.6-1.2 mm, 0.6-0.8 mm, 1.0-3 mm, 1.0-2.8 mm, 1.0-2.5 mm, 1.0-2.2 mm, 1.0-1.8 mm, 1.0-1.5 mm, 1.0-1.2 mm, 1.2-3 mm, 1.2-2.8 mm, 1.2-2.5 mm, 1.2-2.2 mm, 1.2-1.8 mm, 1.2-1.5 mm, 1.5-3 mm, 1.5-2.8 mm, 1.5-2.5 mm, 1.5-2.2 mm, 1.5-1.8 mm, 2.2-3 mm, 2.2-2.8 mm, 2.2-2.5 mm, 2.2-2.4 mm, 2.4-2.8 mm, or 2.4-2.5 mm.

The fibers of the fibrous layer may employ fibers with various lengths. For example, fibers with the same length are used to form a fibrous layer with a uniform thickness when the fibrous layer is formed by the flocking method. For example, the fibrous layer may be formed using fibers with a length of 0.6-3 mm. When the fibrous layer is formed using fibers with such a length, the thickness of the fibrous layer formed on the head part is 0.6-3 mm.

More specifically, the head part 10 has an elliptical (or oval) shape. A fibrous layer with a uniform thickness is formed on the head part with an elliptical shape. The head part with the fibrous layer includes a horizontal long axis portion 101 and a horizontal short axis portion 102.

As used herein while reciting the head part with the fibrous layer of the swab device, the term "horizontal long axis portion" refers to a portion representing the longest axial length among axes perpendicular (or vertical) to the longitudinal axis of the length direction of the swab device in the head part of the swab device having an elliptical shape and the term "horizontal short axis portion" refers to an axis portion other than a portion indicating the longest axial length among axes perpendicular to the longitudinal axis.

According to an embodiment, the head part with the fibrous layer has an elliptical shape and comprises a horizontal long axis portion and a horizontal short axis portion, and wherein the thickness of the head part is 3.8-6.0 mm at the horizontal long axis portion and the thickness of the head part is 2.0-3.5 mm at the horizontal short axis portion.

More specifically, the head part with the fibrous layer has an elliptical shape and comprises a horizontal long axis portion and a horizontal short axis portion, and wherein the thickness of the head part is 4.8-5.2 mm at the horizontal long axis portion and the thickness of the head part is 2.8-3.2 mm at the horizontal short axis portion.

According to an embodiment of the present invention, the fibers of the fibrous layer may have a Dtex value of 3.00-3.50, and more specifically a Dtex value of 3.30-3.35.

The above-described thicknesses and Dtex values of the head part with the fibrous layer allow the swab device to have an appropriate absorbing ability and, when dipped in a specimen transport medium, to have an appropriate releasing ability.

The fibers of the fibrous layer are a substance having hydrophilic properties and is specifically selected from the group consisting of polyesters, polyamides, and cotton.

According to an embodiment, the head part 10 collects 30 μl or more of a specimen. Specifically, the amount of the specimen collected is 30-1500 μl, 30-1200 μl, 30-1000 μl, 30-800 μl, 30-500 μl, 30-300 μl, 30-100 μl, 50-1500 μl, 50-1200 μl, 50-1000 μl, 50-800 μl, 50-500 μl, 50-300 μl, 50-100 μl, 100-1500 μl, 100-1200 μl, 100-1000 μl, 100-800 μl, 100-500 μl, 100-300 μl, 200-1500 μl, 200-1200 μl, 200-1000 μl, 200-800 μl, 200-500 μl, 200-300 μl, 500-1500 μl, 500-1200 μl, 500-1000 μl, 500-800 μl, 800-1500 μl, 800-1200 μl, 800-1000 μl, 1000-1500 μl, or 1000-1200 μl.

(b) The supporting part 11 supports the swab device for collecting a specimen as a whole, and is a part which is gripped by the hand of a specimen collector, and the force of the specimen collector is transmitted to the head part through the supporting part, thereby allowing the specimen to be collected through the head part. The supporting part has a break point 12 formed on the outer surface (or the outer circumferential surface) thereof.

According to an embodiment of the present invention, the supporting part 11 is easily cut at the break point (or cutting groove or cutting point) 12.

The supporting part 11 may be made of a plastic material. For example, it may be made of polypropylene, polyester or polyamide (PA66 or nylon 66).

One of the largest features of the present invention is that the supporting part of the swab device of the present invention includes two positions capable of gripping, i.e., two gripping points. By specifying the two gripping points on the supporting part of the swab device in this way, fine force control with respect to the swab device according to a specimen collection site (for example, nasal cavity or oral cavity) is facilitated, and self sampling by a general person who is a non-expert is enabled as well as sampling by an expert.

The supporting part 11 includes a first gripping point 111 and a second gripping point 112. The first gripping point is located adjacent to the head part. The second gripping point is located closer to the first gripping point and not closer to the head part than the first gripping point. Therefore, the second gripping point is located in the order of the head part, the first gripping point, and the second gripping point on the swab device.

In this specification, the expression "the first gripping point is located adjacent to the head part" may be expressed as "the first gripping point is positioned close to the head part".

As used herein, the term "gripping point" refers to a point or a position at which a specimen collector grips the swab tool.

According to one embodiment, the first gripping point and the second gripping point are each formed as an indication part indicating the gripping point.

According to a specific embodiment of the present invention, the indication part is selected from the group consisting of a dot, a line, a pattern, and a shape capable of being gripped (a grippable shape). Specifically, in the case of dots, lines, and patterns as the indication part indicating the gripping point, dots, lines, and various patterns (e.g., a cross shape, a star shape, a triangle, a quadrangle, etc.) may be displayed on the outer surface of the supporting part in order to display the gripping point. More specifically, the dots, lines, and patterns may be represented by various colors (for example, red, blue, or yellow) known in the art.

According to a more specific embodiment, the first gripping point and the second gripping point are each formed in a shape capable of being gripped (a grippable shape). More specifically, the first gripping point and the second gripping point have a shape capable of being gripped by a finger. Still more specifically, the grippable shape (the shape to be gripped) is a convex shape or a concave shape, and even still more specifically, a concave shape.

FIGS. 6 to 7 show the shape of the gripping point according to one embodiment of the present invention.

In the present specification, a convex shape represents a curvature shape formed in an outer direction of an axis perpendicular to a longitudinal axis based on the longitudinal axis of the swab device, and a concave shape represents a curvature shape formed in an inner direction of an axis perpendicular to the longitudinal axis based on the longitudinal axis of the swab device.

Specifically, the concave-shaped gripping point (see FIGS. 6 and 7) on the supporting part may be formed in a concave shape on the outer surface of the supporting part, and may be formed in a concave shape by applying heat to the gripping point and then applying pressure thereto. More specifically, a protrusion may be formed at the gripping point to prevent slipping of the finger (see FIG. 7).

According to another embodiment of the present invention, the first gripping point is a gripping position for collecting a nasal specimen, and the second gripping point is a gripping position for collecting an oral specimen. More specifically, the first gripping point is a gripping position for collecting a nostril specimen, and the second gripping point is a gripping position for collecting an oral specimen.

Since the area, depth, sensitivity of skin tissue, and a region that can be identified through a mirror are different according to the specimen collection site, the position of gripping (or holding) the supporting part of the swab device may be different. In accordance with the above criteria, the present inventors confirmed that the nasal cavity needs more precise force control than the oral cavity in the specimen collection site, and confirmed that the swab device should be gripped shorter when the nasal cavity specimen is collected or sampled than the oral cavity specimen.

According to an embodiment, the length from the end of the head part to the first gripping point and the length from the end of the head part to the second gripping point have a ratio of 1:1.2-3. Specifically, the length ratio may be 1:1.2-2.5, 1:1.2-2.3, 1:1.2-2.2, 1:1.2-2.0, 1:1.4-2.5, 1:1.4-2.3, 1:1.4-2.2, 1:1.4-2.0, 1:1.5-2.5, 1:1.5-2.3, 1:1.5-2.2, or 1:1.5-2.0. Specifically, the end of the head part represents an end of the head part that is not adjacent to the supporting part.

When the first gripping point and the second gripping point have the above-described length ratio based on the end of the head part, precise force control is possible so that specimens can be collected from two or more sample collection sites through one swap device.

The positions of the first gripping point and the second gripping point adopted in the present invention may be determined based on the break point formed on the supporting part.

According to an embodiment of the present invention, the first gripping point is located between the head part and the break point, and the second gripping point is located between the break point and the end of the supporting part.

In this embodiment, the end of the supporting part represents the end of the supporting part that is not adjacent to the head part.

The swab device of the present embodiment may be confirmed in FIG. 2. Referring to FIG. 2, the swab device of the present embodiment includes a head part, a first gripping point, a break point, and a second gripping point in this order.

According to a more specific embodiment of the present invention, the length from the end of the head part to the first gripping point and the length from the end of the head part to the second gripping point have a ratio of 1:1.8-2.5.

In this embodiment, the end of the head part represents an end of the head part that is not adjacent to the supporting part.

Specifically, the length ratio may be 1:1.8-2.5, 1:1.8-2.3, 1:1.8-2.2, 1:1.8-2.0, 1:1.9-2.5, 1:1.9-2.3, 1:1.9-2.2, 1:1.9-2.0, 1:2.0-2.5, 1:2.0-2.3, or 1:2.0-2.2.

When the first gripping point and the second gripping point have the ratio of the length based on the end of the head part, a precise force control is possible to collect a specimen at two or more specimen collection sites through one swab device.

According to another embodiment of the present invention, the first gripping point and the second gripping point are located between the break point and the end of the supporting part.

In this embodiment, the end of the supporting part represents the end of the supporting part that is not adjacent to the head part.

The swab device of the present embodiment may be confirmed in FIG. 3. Referring to FIG. 3, the swab device of the present embodiment includes a head part, a break point, a first gripping point, and a second gripping point in this order.

According to a more specific embodiment of the present invention, the length from the end of the head part to the first gripping point and the length from the end of the head part to the second gripping point have a ratio of 1:1.2-1.8.

In this embodiment, the end of the head part represents an end of the head part that is not adjacent to the supporting part.

Specifically, the length ratio may be 1:1.2-1.8, 1:1.2-1.7, 1:1.2-1.6, 1:1.2-1.5, 1:1.3-1.8, 1:1.3-1.7, 1:1.3-1.6, 1:1.3-1.5, 1:1.4-1.8, 1:1.4-1.7, 1:1.4-1.6, 1:1.4-1.5, 1:1.5-1.8, 1:1.5-1.7 or 1:1.5-1.6.

When the first gripping point and the second gripping point have the ratio of the length based on the end of the head part, a precise force control is possible to collect a specimen at two or more specimen collection sites through one swab device.

FIG. 8 illustrates a process of collecting nasal and oral swab specimens using the swab device for collecting a specimen of FIGS. 2 and 3, cutting the swab device in a break point, dipping the swab specimen in a specimen transport medium, and transporting the swab specimen to a testing site. Specifically, in the case of collecting a nasal swab specimen using the swab device for collecting a specimen of FIGS. 2 and 3, the specimen is collected by holding the swab device short using the first gripping point, putting the swab device in the nose, gently scraping the nasal walls, and then the swab device is put in a tube including a specimen transport medium, cutting the swab device in the break point, dipping the cut head part, sealing the tube, and transporting the sealed tube to a testing site. In addition, when collecting an oral swab specimen using the swab device for collecting a specimen of FIGS. 2 and 3, the specimen is collected by holding the swab device long using the second gripping point, putting the swab device in the oral cavity, gently scraping the oral walls, and then the swab device is put in a tube including a specimen transport medium, cutting the swab device in the break point, dipping the cut head part, sealing the tube, and transporting the sealed tube to a testing site.

According to an embodiment of the present invention, the supporting part further includes a break point formed on the outer surface thereof.

The positions of the first gripping point and the second gripping point adopted in the present invention may be determined based on two break points formed on the supporting part.

According to an embodiment of the present invention, the break point of the supporting part is a first break point, the first break point is located between the head part and the first gripping point, the supporting part further comprises a second break point, and the second break point is located between the first gripping point and the second gripping point.

The swab device of the present embodiment may be confirmed in FIG. 4. Referring to FIG. 4, the swab device of the present embodiment includes a head part, a first break point, a first gripping point, a second break point, and a second gripping point in this order.

FIG. 9 illustrates a process of collecting nasal and oral swab specimens using the swab device for collecting a specimen of FIG. 4, cutting the swab device in a break point, dipping the swab specimen in a specimen transport medium, and transporting the swab specimen to a testing site. Specifically, in the case of collecting a nasal swab specimen using the swab device for collecting a specimen of FIG. 4, the specimen is collected by holding the swab device short using the first gripping point, putting the swab device in the nose, gently scraping the nasal walls, and then the swab device is put in a tube including a specimen transport medium, cutting the swab device in the first break point, dipping the cut head part, sealing the tube, and transporting the sealed tube to a testing site. In addition, in the case of collecting an oral swab specimen by using the swab device for collecting a specimen of FIG. 4, the specimen is collected by holding the swab device long using the second gripping point, putting the swab device into the oral cavity, gently scraping the oral walls, and then the swab device is put into a tube including a specimen transport medium, cutting the swab device from the second break point, dipping the cut head part, sealing the tube, and transporting the sealed tube to a testing site.

According to a more specific embodiment of the present invention, the length from the end of the head part to the first gripping point and the length from the end of the head part to the second gripping point have a ratio of 1:1.1-1.6.

In this embodiment, the end of the head part represents an end of the head part that is not adjacent to the supporting part.

Specifically, the length ratio may be 1:1.1-1.6, 1:1.1-1.5, 1:1.1-1.4, 1:1.1-1.3, 1:1.1-1.2, 1:1.15-1.6, 1:1.15-1.5, 1:1.15-1.4, 1:1.15-1.3, or 1:1.15-1.2.

When the first gripping point and the second gripping point have the ratio of the length based on the end of the head part, a precise force control is possible to collect a specimen at two or more specimen collection sites through one swab device.

According to a more specific embodiment of the present invention, the length from the end of the head part to the first break point and the length from the end of the head part to the first gripping point have a ratio of 1:1.5-2.5.

In this embodiment, the end of the head part represents an end of the head part that is not adjacent to the supporting part.

Specifically, the length ratio may be 1:1.5-2.5, 1:1.5-2.3, 1:1.5-2.1, 1:1.5-1.9, 1:1.7-2.5, 1:1.7-2.3, 1:1.7-2.1, 1:1.7-1.9, 1:1.8-2.5, 1:1.8-2.3, 1:1.8-2.1, or 1:1.8-1.9.

According to a more specific embodiment of the present invention, the length from the end of the head part to the second break point and the length from the end of the head part to the second gripping point have a ratio of 1:1.2-1.8.

In this embodiment, the end of the head part represents an end of the head part that is not adjacent to the supporting part.

Specifically, the length ratio may be 1:1.2-1.8, 1:1.2-1.7, 1:1.2-1.6, 1:1.2-1.5, 1:1.3-1.8, 1:1.3-1.7, 1:1.3-1.6, 1:1.3-1.5, 1:1.4-1.8, 1:1.4-1.7, 1:1.4-1.6, 1:1.4-1.5, 1:1.5-1.8, 1:1.5-1.7 or 1:1.5-1.6.

According to a more specific embodiment of the present invention, the length from the end of the head part to the first break point and the length from the end of the head part to the second break point have a ratio of 1:1.8-2.5.

In this embodiment, the end of the head part represents an end of the head part that is not adjacent to the supporting part.

Specifically, the length ratio may be 1:1.8-2.5, 1:1.8-2.4, 1:1.8-2.3, 1:2.0-2.5, 1:2.0-2.4, 1:2.0-2.3, 1:2.2-2.5, 1:2.2-2.4, or 1:2.2-2.3.

According to an embodiment, the head part and the supporting part may have a length ratio of 1:5-15. Specifically, the length ratio may be 1:5-15, 1:5-13, 1:5-11, 1:5-9, 1:7-15, 1:7-13, 1:7-11, 1:7-9, 1:9-15, 1:9-13, or 1:9-11.

According to an embodiment of the present invention, the total length of the swab device is 140-180 mm. Specifically, the total length of the swab device 100 may be 140-180 mm, 140-176 mm, 140-172 mm, 140-168 mm, 140-164 mm, 140-160 mm, 144-180 mm, 144-176 mm, 144-172 mm, 144-168 mm, 144-164 mm, 144-160 mm, 148-180 mm, 148-176 mm, 148-172 mm, 148-168 mm, 148-164 mm, 148-160 mm, 152-180 mm, 152-176 mm, 152-172 mm, 152-168 mm, 152-164 mm, 152-160 mm, 156-180 mm, 156-176 mm, 156-172 mm, 156-168 mm, 156-164 mm, 156-160 mm, 160-180 mm, 160-176 mm, 160-172 mm, 160-168 mm or 160-164 mm.

According to another embodiment of the present invention, the length of the head part is 14-18 mm. Specifically, the length of the head part 10 may be 14-18 mm, 14-17 mm, 14-16 mm, 15-18 mm, 15-17 mm, 15-16 mm, 16-18 mm or 16-17 mm.

When the head part has the length, the swab device can collect a specimen (or sample) by directly contacting with the sample collection site.

According to another embodiment of the present invention, the length of the supporting part is 120-160 mm. Specifically, the length of the supporting part 11 is 120-160 mm, 120-156 mm, 120-152 mm, 120-148 mm, 120-144 mm, 124-160 mm, 124-156 mm, 124-152 mm., 124-148 mm, 124-144 mm, 128-160 mm, 128-156 mm, 128-152 mm, 128-148 mm, 128-144 mm, 132-160 mm, 132-156 mm, 132-152 mm, 132-148 mm, 132-144 mm, 136-160 mm, 136-156 mm, 136-152 mm, 136-148 mm, 136-144 mm, 140-160 mm, 140-156 mm, 140-152 mm, 140-148 mm, 140-144 mm, 144-160 mm, 144-156 mm, 144-152 mm, or 144-148 mm.

When the supporting part has the above length, the supporting part may entirely support the swab device for collecting a specimen.

According to an embodiment, the swab device is a swab device for collecting respiratory specimens, specifically a swab device for collecting nasal and oral specimens, and more specifically a swab device for collecting nostril and oral specimens.

In still another aspect of the present invention, there is provided a kit for collecting a specimen to detect a respiratory pathogen, comprising:

(a) the above-described swab device for collecting a specimen of the present invention; and (b) a container comprising a specimen transport medium.

Since the kit for collecting a specimen of the present invention includes the above-described swab device for collecting a specimen of the present invention, the common descriptions between them are omitted in order to avoid undue redundancy leading to the complexity of the present specification.

According to an embodiment, the kit for collecting a specimen is a self-sampling kit.

According to an embodiment of the present invention, the specimen transport medium is a cell maintenance buffer and a cell inactivation buffer.

According to an embodiment, the cell maintenance buffer is a saline-based solution or a balanced salt solution-based buffer.

According to an embodiment of the present invention, the saline-based solution is a phosphate buffered saline (PBS) or a normal saline.

According to an embodiment, the cell inactivation buffer comprises (i) a chaotropic agent. More specifically, the cell inactivation buffer further comprises at least one ingredient selected from the group consisting of (ii) a detergent; (iii) a chelator; (iv) a buffer; and (v) a reducing agent.

According to an embodiment of the present invention, the specimen transport medium is used in a nucleic acid amplification reaction without nucleic acid isolation process when a specimen collected by the swab device for collecting a specimen is immersed in the specimen transport medium.

Optionally, the specimen transport medium further comprises a pH indicator (e.g., phenol red, bromocresol purple, and bromothymol blue).

In another aspect of the present invention, there is provided a kit for detecting a respiratory pathogen, comprising:

(a) the above-described kit for collecting a specimen of the present invention; and (b) a real-time nucleic acid amplification reaction composition comprising (i) primers for amplifying a nucleic acid molecule of the respiratory pathogen; (ii) a probe hybridizing with the nucleic acid molecule of the respiratory pathogen; and (iii) an enzyme including a DNA polymerase.

Since the kit for detecting a respiratory pathogen of the present invention includes the above-described kit for collecting a specimen of the present invention, the common descriptions between them are omitted in order to avoid undue redundancy leading to the complexity of the present specification.

According to an embodiment, the enzyme includes a hot-start Taq polymerase and a reverse transcriptase.

According to an embodiment of the present invention, the nucleic acid amplification reaction composition further comprises primers for amplifying an endogenous IC and an exogenous IC.

According to an embodiment, the endogenous IC is a RNase P gene, a beta-globin gene, a GAPDH gene, a beta-actin gene, a PPIA gene, a RPS9 gene, a RPS15A gene, or an UXT gene, and the exogenous IC is a bacteriophage MS2 or an armoured RNA.

According to an embodiment of the present invention, the respiratory pathogen is a respiratory virus and/or a respiratory bacterium. More specifically, the respiratory virus is an influenza virus, a respiratory syncytial virus (RSV), an adenovirus, an enterovirus, a parainfluenza virus (PIV), a metapneumovirus (MPV), a bocavirus, a rhinovirus and/or a coronavirus. More specifically, the coronavirus is a severe acute respiratory syndrome coronavirus 2 (SARS-CoV-2).

According to an embodiment, the nucleic acid molecule of the respiratory pathogen is at least one gene of a RdRP gene, a S gene, and a N gene of SARS-CoV-2.

In still another aspect of the present invention, there is provided a method for collecting a specimen to detect a respiratory pathogen, comprising:

(a) obtaining a nasal swab specimen and an oral swab specimen by using the above-described kit for collecting a specimen of the present invention; and (b) immersing the nasal swab specimen and the oral swab specimen in a specimen transport medium included in one container.

Since the method for collecting a specimen of the present invention employs the kit for collecting a specimen of the present invention, the common descriptions between them are omitted to avoid undue redundancy leading to the complexity of the present specification.

In still another aspect of the present invention, there is provided a method for detecting a respiratory pathogen, comprising:

(a) performing a nucleic acid amplification reaction by using a nucleic acid amplification reaction composition and a specimen transport medium in which a nasal swab specimen and an oral swab specimen collected by the above-described swab device for collecting a specimen of the present invention are dipped together; and (b) determining the presence or absence of the respiratory pathogen by analyzing the results of the nucleic acid amplification reaction.

Since the method for detecting a respiratory pathogen of the present invention employs the above-described swab device for collecting a specimen of the present invention, the common descriptions between them are omitted to avoid undue redundancy leading to the complexity of the present specification.

The detection method of the present invention will be described in detail according to each step as follows.

Step (a): Nucleic Acid Amplification Reaction Using Nasal Swab Specimen and Oral Swab Specimen First, a nucleic acid amplification reaction is performed by using a nucleic acid amplification reaction composition and a specimen transport medium in which a nasal swab specimen and an oral swab specimen collected by the above-described swab device for collecting a specimen of the present invention are dipped together.

The specimen used in the present invention is a respiratory swab specimen, specifically a nasal swab specimen and an oral swab specimen, and more specifically a nostril swab specimen and an oral swab specimen.

As used herein, the term "nasal swab specimen" refers to a swab specimen, which is obtained by applying the swab device to nasal cavities and onto which a biopsy specimen from the nasal cavities is adsorbed, and the term is distinguished from a nasopharyngeal swab specimen. Specifically, the nasal cavity is a nostril or a nostril cavity. For example, referring to FIG. 10, a swab device is inserted into the nostril (e.g., insert 2-3 cm) and then a biopsy specimen is collected from the inner portion of the nostril while the swab is smoothly rotated for 10-15 seconds.

According to an embodiment, the nasal swab specimen is obtained by applying one swab device to both of two nasal cavities.

The oral swab specimen used in the present invention may include a specimen obtained by applying a swab device to the oral cavity.

As used herein, the term "oral swab specimen" refers to a specimen obtained by applying a swab device to the oral cavity to collect saliva and/or epithelial cells of the wall of the oral cavity. Specifically, the oral swab specimen represents a specimen obtained by applying a swab device to the oral cavity to collect saliva (i.e., a saliva swab specimen).

According to an embodiment of the present invention, the oral swab specimen is obtained by applying the swab device to a supralingual part, a sublingual part, or an oral wall (i.e., the wall of the oral cavity).

For example, the oral swab specimen may be obtained by applying a swab device to the surface of the tongue to allow saliva to be sufficiently absorbed into a fibrous layer of the swab device or collecting saliva from the end of the tongue and then allowing the saliva to be sufficiently absorbed into a fibrous layer of the swab device (see FIG. 11), or rubbing a swab device on the wall of the oral cavity to allow saliva to be sufficiently absorbed into a fibrous layer and thus allow epithelial cells to be adsorbed on the fibrous layer.

Alternatively, the oral swab specimen may be obtained by allowing saliva to sufficiently be absorbed while swabbing the sublingual part (see FIG. 11).

According to an embodiment of the present invention, the oral swab specimen is obtained by applying the swab device to the sublingual part.

According to an embodiment, the oral swab specimen may be obtained by applying a swab device to the inside of cheek, the gingiva and/or palate.

The term "saliva swab specimen" is used interchangeably with an oral swab specimen or oral saliva specimen so long as the oral swab specimen or oral saliva specimen is also obtained by applying a swab device to a part described above in order to mainly collect saliva.

According to an embodiment of the present invention, the nasal swab specimen and the oral swab specimen are obtained by applying two swab devices to a nasal cavity and an oral cavity, respectively. Alternatively, the nasal swab specimen and the oral swab specimen are obtained by applying one swab device to a nasal cavity and then an oral cavity.

According to an embodiment, the nasal swab specimen and the oral swab specimen are obtained through self-sampling. The nasal swab specimen and the oral swab specimen may be easily obtained by an ordinary person without the involvement of experts, and thus a valid specimen necessary for molecular diagnosis may also be obtained by self-sampling.

Since the swab device for collecting a nasal swab specimen and an oral swab specimen uses the above-described swab device for collecting a specimen of the present invention, the common descriptions between them are omitted in order to avoid undue redundancy leading to the complexity of the present specification.

The nasal swab and oral swab completing specimen collection are dipped, that is, immersed in a specimen transport medium included in the container. The specimens included in the swabs are released to the specimen transport medium by such dipping. In general, the container comprising the specimen transport medium with the swabs dipped therein is transported to a place where a nucleic acid amplification reaction is performed.

The descriptions of the specimen transport medium in the method of the present invention are applied in the same manner to the specimen transport medium included in the above-described kit for collecting a specimen of the present invention.

The specimen transport medium being usable in the present invention includes two types of buffers: a cell maintenance buffer and a cell inactivation buffer (i.e., a cell lysis buffer).

As used herein, the term “cell maintenance buffer” refers to a buffer which maintains cells in a specimen such that the cells are not lysed.

The cell maintenance buffer usable in the present invention includes any cell maintenance buffer that is commonly used in the art. According to an embodiment of the present invention, the cell maintenance buffer is a saline-based solution or a balanced salt solution-based buffer.

More specifically, the saline-based solution used in the present invention is phosphate buffered saline (PBS) or normal saline.

The balanced salt solution-based buffer used in the present invention may include a balanced salt solution that is commonly used in the art. Examples of the balanced salt solution comprise Alsever’s solution, Earle’s balanced salt solution, Gey’s balanced salt solution, Hanks’ balanced salt solution, Puck’s balanced salt solution, Ringer’s balanced salt solution, Simm’s balanced salt solution, and Tyrode’s balanced salt solution.

The balanced salt solution-based buffer used in the present invention may comprise other ingredients in addition to the above-descried balanced salt solution. For example, the other ingredients include bovine serum albumin, cysteine, sucrose, and glutamic acid.

The cell inactivation buffer, that is, a cell lysis buffer, used in the present invention is a buffer which lyses a specimen, for example, a virus, to allow a nucleic acid molecule in the virus to be released to the buffer, denatures protein components, inactivates DNase and RNase, and maintains the integrity of the nucleic acid molecule.

More specifically, the cell inactivation buffer as a specimen transport medium used in the present invention comprises (i) a chaotropic agent, and still more specifically, further comprises, in addition to (i) a chaotropic agent, at least one ingredient selected from the group consisting of (ii) a detergent; (iii) a chelator; (iv) a buffer; and (v) a reducing agent, and still more specifically, comprises (ii) a detergent; (iii) a chelator; (iv) a buffer; and (v) a reducing agent, in addition to (i) a chaotropic agent.

Examples of the chaotropic agent include guanidine thiocyanate, guanidine isocyanate, guanidine hydrochloride, and potassium thiocyanate, and more specifically, the chaotropic agent is guanidine thiocyanate. The chaotropic agent opens microbial cells to induce cell lysis and allow DNA and RNA to be released, and prevents nucleic acid molecules from being degraded by nuclease.

Specifically, the detergent is sodium dodecyl sulfate, lithium dodecyl sulfate, sodium taurodeoxycholate, sodium taurocholate, sodium glycocholate, sodium deoxycholate, sodium cholate, sodium alkylbenzene sulfonate, polysorbate, Triton X-100, or N-lauroyl sarcosine.

Specifically, the chelator is ethylene glycol tetraacetic acid, hydroxyethylethylenediaminetriacetic acid, diethylene triamine pentaacetic acid, N,N-bis(carboxymethyl)glycine, ethylenediaminetetraacetic, citrate anhydrous, sodium citrate, calcium citrate, ammonium citrate, ammonium bicitrate, citric acid, diammonium citrate, ferric ammonium citrate, or lithium citrate.

Specifically, examples of the buffer include tris(hydroxymethyl)aminomethane, citrate, 2-(N-morpholino)ethanesulfonic acid, N,N-Bis(2-hydroxyethyl)-2-aminoethanesulfonic acid, 1,3-bis(tris(hydroxymethyl)methyl amino) propane, 4-(2-hydroxyethyl)-1-piperazine ethanesulfonic acid, 3-(N-morpholino)propanesulfonic acid, hydroxyethyl piperazine ethane sulfonic acid, bicarbonate, and phosphate.

Specifically, examples of the reducing agent include 2-mercaptoethanol, tris(2-carboxyethyl)phosphine, dithiothreitol, dimethylsulfoxide, and sodium hydroxide.

In the specimen transport medium used in the present invention, the chaotropic agent may be comprised at an amount of 5-30 parts by weight relative to 100 parts by weight of the medium, and the detergent, the chelator, the buffer, and the reducing agent may be comprised at amounts of 1-15 parts by weight, 0.1-5 parts by weight, 2-10 parts by weight, and 0.1-3 parts by weight, respectively.

According to an embodiment of the present invention, the cell inactivation buffer as a specimen transport medium has an inactivation function by lysis of a respiratory infection pathogen and a stabilization function of a nucleic acid material (specifically, DNA or RNA, and more specifically RNA) released from the lysed pathogen.

Optionally, the specimen transport medium further includes a pH indicator (e.g., phenol red, bromocresol purple, and bromothymol blue), and more specifically phenol red. The pH indicator makes it possible to monitor whether the specimen transport medium is infected with bacteria.

A nucleic acid amplification reaction is performed using the specimen transport medium. The specimen transport medium may be applied to a nucleic acid amplification in three manners.

According to the first manner, the specimen transport medium is directly applied to a nucleic acid amplification reaction without any pretreatment. For example, the specimen transport medium may be added to a nucleic acid amplification reaction composition to perform PCR by an ordinary direct PCR method.

According to the second manner, the specimen transport medium is subjected to heat treatment (incubation), and then the incubation resultant is applied to a nucleic acid amplification reaction.

Specifically, the specimen transport medium in which the nasal swab specimen and the oral swab specimen are dipped together is subjected to incubation at 60° C. to 100° C. (more specifically, 95° C. to 100° C.) for 1-15 minutes before used in the nucleic acid amplification reaction, and the nucleic acid amplification reaction was performed using the incubation resultant. In such a case, the specimen transport medium used in the nucleic acid amplification reaction may be diluted to 2 to 10 times (more specifically, 3 to 5 times) before or after the incubation, and then applied to the nucleic acid amplification reaction.

According to the third manner, the specimen transport medium in which a nasal swab specimen and an oral swab specimen are dipped together is subjected to a nucleic acid isolation process before used in a nucleic acid amplification reaction, and the nucleic acid amplification reaction is performed using the nucleic acid molecule isolated by the nucleic acid isolation process.

The nucleic acid isolation process may be performed by, for example, a magnetic particle-based isolation method (see U.S. Pat. Nos. 6,027,945 and 7,517,969). For example, the nucleic acid molecule can be isolated by sequentially using buffers for nucleic acid molecule isolation, including a lysis buffer, a binding buffer, a washing buffer, and a release buffer. More specifically, the specimen transport medium is treated with a lysis buffer comprising a chaotropic agent (e.g., guanidine thiocyanate) and a detergent (e.g., Tween-20) to lyse viruses or bacteria in the specimen, the lysis product is treated with a binding buffer containing magnetic particles to bind the nucleic acid molecules to the surface of the magnetic particles, the magnetic particles are washed with a washing buffer containing ethanol, and then the magnetic particles are treated with a release buffer to isolate the nucleic acid molecules bound to the surface of the magnetic particles.

In the nucleic acid amplification reaction, a probe and primers hybridizing with a target may be used.

The probe or primers used in the present invention have sequences complementary to a target nucleotide sequence. As used herein, the term "complementary" refers to having complementarity at the extent of being selectively hybridizable with the above-described nucleotide sequence under specific hybridization or annealing conditions. Therefore, the term "complementary" has a different meaning from the term "perfectly complementary", and the primers or probe of the present invention may have one or more mismatch nucleotide sequences as long as the primers or probe is selectively hybridizable with the above nucleotide sequence.

As used herein, the term "primer" refers to a single-strand oligonucleotide capable of acting as an initial point of template-directed DNA synthesis at an appropriate temperature in an appropriate buffer under appropriate conditions (i.e., four types of different nucleoside triphosphates and polymerase). An appropriate length of the primers may vary according to various factors, for example, temperature and use of the primers, but the primers are typically 15 to 40 nucleotides in length. A short primer molecule generally requires a lower temperature in order to form a sufficiently stable hybrid complex with a template.

The sequence of the primer is not required to have a perfectly complementary sequence to a partial sequence of the template, and it is enough that the sequence of the primer may have sufficient complementarity within a range in which the primer can do an intrinsic action when hybridized with the template. Therefore, the primers of the present invention do not need to have a perfectly complementary sequence to the above-described nucleotide sequence as a template, and it is sufficient that the primers have sufficient complementarity within a range in which the primers can be hybridized with the gene sequence to act as primers. Such primers can be designed with reference to the above-described nucleotide sequence by a person skilled in the art, and for example, the design may be carried out using a computer program for primer design (e.g., PRIMER 3 program).

As used herein, the term "probe" refers to natural or modified monomers or linear oligomers of linkages, and the probe includes deoxyribonucleotides and ribonucleotides, can specifically hybridize with a target nucleotide sequence, and is naturally present or artificially synthesized. The probe of the present invention is preferably in a single-stranded form, and is an oligodeoxyribonucleotide.

As used herein, the term "amplification" refers to a reaction of amplifying nucleic acid molecules. A variety of amplification reactions have been reported in the art, including polymerase chain reaction (PCR, U.S. Pat. Nos. 4,683,195, 4,683,202, and 4,800,159), reverse transcription-polymerase chain reaction (RT-PCR, Sambrook et. al., Molecular Cloning. A Laboratory Manual, 3rd ed. Cold Spring Harbor Press (2001)), methods by Miller, H. I. (WO 89/06700) and Davey, C. et al., (EP 329,822), ligase chain reaction (LCR), Gap-LCR (WO 90/01069), repair chain reaction (EP 439,182), transcription-mediated amplification (TMA, WO 88/10315), self-sustained sequence replication (WO 90/06995), selective amplification of target polynucleotide sequences (U.S. Pat. No. 6,410,276), consensus sequence primed polymerase chain reaction (CP-PCR, U.S. Pat. No. 4,437,975), arbitrarily primed polymerase chain reaction (AP-PCR, U.S. Pat. Nos. 5,413,909 and 5,861,245), nucleic acid sequence based amplification (NASBA, U.S. Pat. Nos. 5,130,238, 5,409,818, 5,554,517, and 6,063,603), strand displacement amplification, and loop-mediated isothermal amplification (LAMP), but is not limited thereto. Other usable amplification methods are disclosed in U.S. Pat. Nos. 5,242,794, 5,494,810, and 4,988,617, and U.S. patent application Ser. No. 09/854,317.

PCR is the most well-known method for nucleic acid amplification, and modifications and applications thereof have been developed. For example, for improving PCR specificity or sensitivity, touchdown PCR, hot start PCR, nested PCR, and booster PCR have been developed by modifying the conventional PCR procedure. In addition, real-time PCR, differential display PCR (DD-PCR), rapid amplification of cDNA ends (RACE), multiplex PCR, inverse polymerase chain reaction (IPCR), Vectorette PCR, and thermal asymmetric interlaced PCR (TAIL-PCR) have been suggested for specific applications. The details of PCR are disclosed in McPherson, M. J., and Moller, S. G. PCR. BIOS Scientific Publishers, Springer-Verlag New York Berlin Heidelberg, N.Y. (2000), the teachings of which are incorporated herein by reference.

Most of respiratory pathogens have RNA as genome. In such a case, a gene amplification reaction is performed using primers to be annealed to RNA or cDNA while RNA in a sample is used as a template. cDNA is synthesized from the isolated RNA, and the cDNA is amplified. cDNA can be easily synthesized using reverse transcriptase (see PNAS USA, 85: 8998 (1988); Libert F, et al., *Science,* 244: 569 (1989); and Sambrook, J. et al., *Molecular Cloning.* A Laboratory Manual, 3rd ed. Cold Spring Harbor Press (2001)). Then, the synthesized cDNA is amplified through a gene amplification reaction.

The primers used for the present invention is hybridized or annealed to a region of the template to form a double-chain structure. The nucleic acid hybridization conditions suitable for forming such a double-chain structure are disclosed in Joseph Sambrook, et al., Molecular Cloning, A Laboratory Manual, Cold Spring Harbor Laboratory Press, Cold Spring Harbor, N.Y. (2001), and Haymes, B. D., et al., Nucleic Acid Hybridization, A Practical Approach, IRL Press, Washington, D.C. (1985).

A variety of DNA polymerases may be used in the amplification of the present invention, and include "Klenow" fragment of *E. coli* DNA polymerase I, a thermostable DNA polymerase, and bacteriophage T7 DNA polymerase. Particularly, the polymerase is a thermostable DNA polymerase obtained from a variety of bacterial species, including *Thermus aquaticus* (Taq), *Thermus thermophilus* (Tth), *Thermus filiformis, Thermis flavus, Thermococcus literalis*, and *Pyrococcus furiosus* (Pfu).

When a polymerization reaction is performed, the ingredients necessary for the reaction are preferably provided in excess to a reaction container. The excess with respect to the ingredients necessary for the amplification reaction means amounts of the ingredients that the amplification reaction is not substantially restricted by the concentrations of the ingredients. A cofactor such as $Mg^{2+}$, and dATP, dCTP, dGTP and dTTP are required to be provided to the reaction mixture to an extent that a desired degree of amplification can be achieved. All the enzymes used in the amplification reaction may be in an active state under the same reaction conditions. Indeed, a buffer allows all enzymes to be under conditions near optimal reaction conditions. Therefore, the amplification of the present invention may be performed in a single reaction material without changing conditions, such as the addition of a reaction material.

According to an embodiment of the present invention, the nucleic acid amplification reaction used in the present invention is a real-time nucleic acid amplification reaction.

The real-time nucleic acid amplification reaction may be performed using a non-specific fluorescence dye that is non-specifically intercalated into a duplex, which is an amplicon of the target nucleic acid sequence.

In addition, the real-time nucleic acid amplification reaction may use a labeled probe specifically hybridizing with the target nucleic acid sequence. Examples of such a method include the molecular beacon method using a dual-labeled probe forming a hair-pin structure (Tyagi et al, Nature Biotechnology v. 14 Mar. 1996), a hybridization probe method using two probes single-labeled with a donor or an acceptor (Bernad et al, 147-148 Clin Chem 2000; 46), a Lux method using a single-labeled oligonucleotide (U.S. Pat. No. 7,537,886), and a TaqMan method using a cleavage reaction of a double-labeled probe by 5'-nuclease activity of DNA polymerase as well as the hybridization of a dual-labeled probe (U.S. Pat. Nos. 5,210,015 and 5,538,848), but are not limited thereto.

In addition, the real-time nucleic acid amplification reaction may be performed using a duplex dependently formed on the presence of the target nucleic acid sequence. The duplex dependently formed on the presence of the target nucleic acid sequence is not an amplicon itself of the target sequence formed by the amplification reaction, but the duplex that the amount of the duplex increases in proportion to the amplification of the target nucleic acid sequence. The duplex formed depending on the presence of the target nucleic acid sequence may be obtained by various methods, for example, PTO cleavage and extension (PTOCE) method disclosed in WO 2012/096523, the contents of which are incorporated herein by reference.

According to an embodiment, the nucleic acid amplification reaction composition comprises primers, a probe, and an enzyme. The nucleic acid amplification reaction composition comprises a buffer, dNTP, KCl, and $MgCl_2$. For example, the nucleic acid reaction composition may contain 40 mM Tris. CI (pH 8.8), 100 mM KCl, 4 mM $MgCl_2$, and 400 μM dNTP. The enzymes included in the nucleic acid amplification reaction composition of the present invention include Taq DNA polymerase (specifically, hot-start Taq DNA polymerase) and reverse transcriptase, and more specifically hot-start Taq DNA polymerase, reverse transcriptase, uracil DNA glycosylase (UDG), and RNase inhibitor (RI). The hot-start Taq DNA polymerase includes chemically-modified hot-start Taq DNA polymerase (see: Paul N, et al., Hot start PCR. Methods in Molecular Biology. Humana Press. 630:301-18 (2010)), antibody-based hot start Taq DNA polymerase (Paul N, et al., Hot start PCR. Methods in Molecular Biology. Humana Press. 630:301-18 (2010)), and aptamer-based hot-start Taq DNA polymerase (Birch D E, et al., Simplified hot start PCR. *Nature* 381: 445-446 (1996)). The reverse transcriptase used in the present invention is a reverse transcriptase conventionally used in the art, and specifically, MMLV-based thermally stable reverse transcriptase.

According to an embodiment of the present invention, the nucleic acid amplification reaction composition comprises primers, a probe, and an enzyme (hot-start Taq DNA polymerase, MMLV-based thermally stable reverse transcriptase, and UDG).

An internal control (IC) is generally used in the nucleic acid amplification reaction to determine the validity of the nucleic acid amplification reaction. In the present invention, the validity of sampling of nostril and oral swab specimens as well as the nucleic acid amplification reaction can be determined using two types of ICs.

According to an embodiment, the nucleic acid amplification reaction composition comprises primers for amplifying the nucleic acid molecule of the respiratory pathogen, endogenous IC, and exogenous IC, wherein the endogenous IC is used to determine the validity of sampling of nostril and oral swab specimens and the exogenous IC is used to determine the validity of the nucleic acid amplification reaction.

According to an embodiment of the present invention, the endogenous IC is a RNase P gene, a beta-globin gene, a GAPDH gene, a beta-actin gene, a PPIA gene, a RPS9 gene, a RPS15A gene, or an UXT gene, and the exogenous IC is a bacteriophage MS2 or an armoured RNA.

Step (b): Determining Presence or Absence of Respiratory Pathogen

Finally, the presence or absence of the respiratory pathogen is determined by analyzing the results of the nucleic acid amplification reaction.

For example, when a signal above a particular threshold value is observed in the real-time detection of signals during the real-time nucleic acid amplification reaction, it is determined that a respiratory pathogen is present.

According to an embodiment of the present invention, the respiratory pathogen detected by the present invention include respiratory viruses and/or respiratory bacteria.

For example, the present invention determines infections with influenza viruses (e.g., influenza A virus and influenza B virus), respiratory syncytial viruses (RSV) (e.g., RSV A and RSV B), adenoviruses, enteroviruses, parainfluenza viruses (PIV) (e.g., PIV 1, PIV 2, PIV 3, and PIV 4), metapneumoviruses (MPV), bocaviruses, rhinoviruses, coronaviruses (e.g., CoV NL63, CoV 229E, CoV OC43, CoV HKU1, SARS-COV, MERS-CoV, SARS-CoV-2), *Mycoplasma pneumoniae, Chlamydophila pneumoniae, Legionella pneumophila, Haemophilus influenzae, Streptococcus pneumoniae, Bordetella pertussis* and/or *Bordetella parapertussis.*

According to an embodiment, the present invention determines infections with respiratory viruses including influenza viruses, respiratory syncytial viruses (RSV), adenoviruses, enteroviruses, parainfluenza viruses (PIV), metapneumoviruses (MPV), bocaviruses, rhinoviruses, and/or coronaviruses.

More specifically, the method of the present invention determines an infection with severe acute respiratory syndrome coronavirus 2 (SARS-CoV-2).

According to an embodiment of the present invention, the nucleic acid amplification reaction composition comprises primers, which are used to amplify at least one, more specifically at least two, and still more specifically three genes among RdRP gene, S gene, and N gene of SARS-CoV-2, and when at least one of the RdRP gene, S gene, and N gene is measured to be positive, it is determined that a pathogen of SARSCoV-2 is present.

According to an embodiment, the present invention is performed by a real-time nucleic acid amplification reaction showing a limit of detection (LoD) value of 100-500 RNA copies/reaction.

Effects of the Invention

The features and advantages of the present invention are summarized as follows:

(a) Conventional swab devices for collecting a specimen have the shape, structure and/or length that allow specimens to be collected only at a specific specimen collection site, so that a kit collecting specimens at two specimen collection sites should include swab devices for collecting a specimen suitable for a specific specimen collection site. This is not only limited in performing self-sampling by ordinary persons as non-experts, but also has a problem in economic efficiency because swab devices having two different shapes, structures, and/or lengths should be included in forming one package of a kit for collecting a specimen.

(b) The present invention forms two positions capable of gripping in one swab device, i.e., two gripping points to easily perform precise force control for the swab device according to a specimen collection site (for example, nasal cavity or oral cavity), so that a swab specimen can be accurately and easily collected at the specimen collection site, and a specimen amount sufficient to detect respiratory pathogens can be collected.

(c) In addition, the swab device of the present invention can be used not only for sampling by experts but also for self sampling by ordinary persons as non-experts, and respiratory pathogens can be detected from the collected specimens.

The present invention will now be described in further detail by examples. It would be obvious to those skilled in the art that these examples are intended to be more concretely illustrative and the scope of the present invention as set forth in the appended claims is not limited to or by the examples.

EXAMPLES

Figure 1:
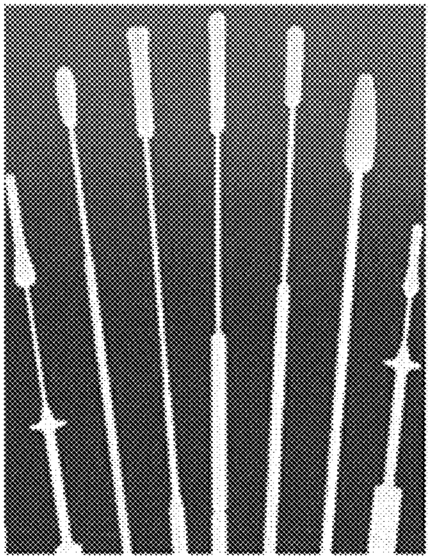
FIG. 1 shows conventional swab devices for collecting a specimen having different shapes, structures, and/or lengths according to specimen collection sites.
Figure 2:
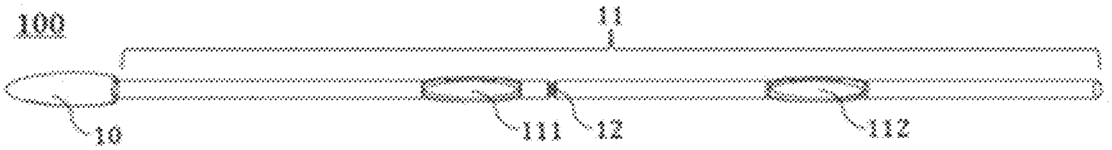
FIGS. 2, 3 and 4 show swab devices for collecting a specimen according to an embodiment of the present invention.

Comparative Example 1: Detection of SARS-CoV-2 by Collecting Nostril Swab Specimen and Oral Swab Specimen The nasopharyngeal and oropharyngeal swab specimens were collected by using swab devices for collecting the nasopharyngeal swab specimen and the oropharyngeal swab specimen (Copan Company) included in package 1 of a kit for collecting a specimen among swab devices for collecting a specimen shown in FIG. 1.

Then, the nasopharyngeal swab specimen and the oropharyngeal swab specimen were immersed together in a clinical virus transport medium (CTM) (Noble Bio) or UTM (Copan) specimen transport medium, which is a balanced salt solution-based buffer. Then, the specimen transport medium was subjected to heat treatment or nucleic acid isolation to obtain a target nucleic acid, which is to be added to RT-PCR reactants.

To obtain the target nucleic acid by heat treatment, the specimen transport medium in which the nasopharyngeal swab specimen and the oropharyngeal swab specimen were immersed was diluted to three times, and incubated at 98° C. for 3 minutes, thereby obtaining the target nucleic acid (hereinafter, referred to as "crude nucleic acid").

The nucleic acid isolation was carried out using the STARMag 96×4 Universal Cartridge Kit (Cat. No. 744300.4. UC384, Seegene Inc.) and the automatic nucleic acid extraction system, Microlab NIMBUS (Cat. No. 65415-02, Hamilton). The nucleic acid isolation was conducted according to the manual from the manufacturer of nucleic acid isolation reagents and the operation manual of the system. The nucleic acid isolation was conducted using 300 μl of the specimen transport medium in which the nasopharyngeal swab specimen and the oropharyngeal swab specimen were immersed (hereinafter, "isolated nucleic acid").

The RT-PCR reaction using the crude nucleic acid or isolated nucleic acid was performed using Allplex™ SARS-CoV-2 Assay (Seegene Inc.), which is a multiple one-step RT-PCR product. The Allplex™ SARS-CoV-2 Assay product is a one-step RT-PCR product for detecting a target gene (E gene) of both Sarbecovirus and SARS-CoV-2 and target genes (RdRP gene, S gene, and N gene) of SARS-CoV-2.

A reaction mixture of the RT-PCR reaction having a final volume of 20 μl was prepared using 5 μl of the crude nucleic acid or the isolated nucleic acid, 5 μl of enzymes (including chemically modified hot-start Taq polymerase, RTase, UDG, and RI), 5 μl of RNase-free Water, and 5 μl of SARS2 MOM (Oligo mix).

Each tube containing the prepared reaction mixture was placed in a real-time thermocycler (CFX96, Bio-Rad), and then reacted at 50° C. for 20 minutes, denatured at 95° C. for 15 minutes, followed by repeating 45 cycles of 10 seconds at 95° C., 15 seconds at 60° C., and 10 seconds at 72° C. The experiment was repeated twice to obtain an average Ct value.

As a result of the experiment, the use of the isolated nucleic acid obtained from the nasopharyngeal swab specimen and the oropharyngeal swab specimen could obtain a positive signal for SARS-CoV-2. In addition, the use of the crude nucleic acid from the nasopharyngeal swab specimen and the oropharyngeal swab specimen could also obtain a positive signal for SARS-CoV-2, but showed a Ct value delayed by about 1-3 compared with the isolated nucleic acid, indicating a small drop of sensitivity by about 3-6 times.

Example 1: Detection of SARS-CoV-2 by Collecting Nostril Swab Specimen and Oral Swab Specimen Using the two swab devices for collecting a specimen shown in FIG. 3 included in package 1 of a kit for collecting a specimen, the nostril swab specimen and the oral swab specimen were collected to detect SARS-CoV-2. The swab device for collecting a specimen of FIG. 3 has a total length of 160 mm, a head part length of 16 mm, and a supporting part length of 144 mm. Further, in the swab device of FIG. 3, lengths from the end of the head part, which is not adjacent to the supporting part, to the break point, to the first gripping point, and to the second gripping point are 60 mm, 80 mm, and 120 mm, respectively.

Figure 3:
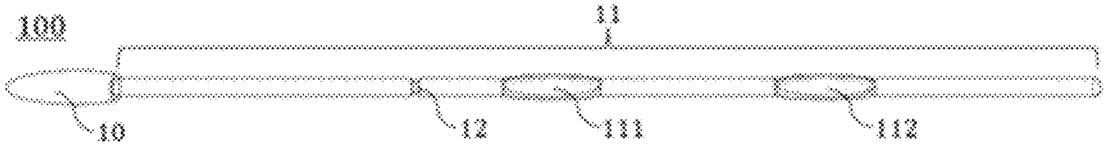
Figure 4:
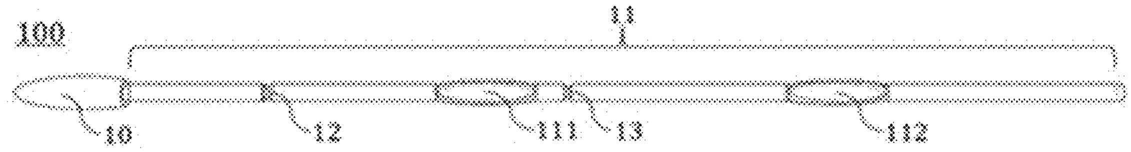
Figure 5:
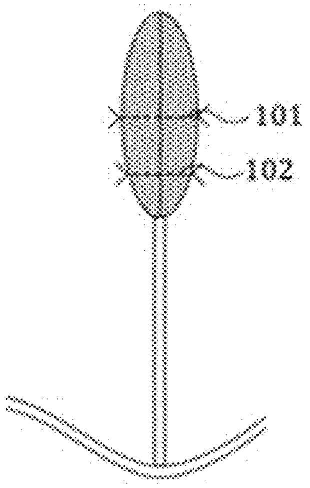
FIG. 5 shows a head part of a swab device for collecting a specimen according to an embodiment of the present invention.
Figure 6:
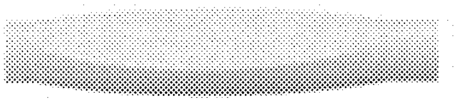
FIGS. 6 to 7 show a shape of a gripping point according to one embodiment of the present invention.
Figure 7:
Figure 8:
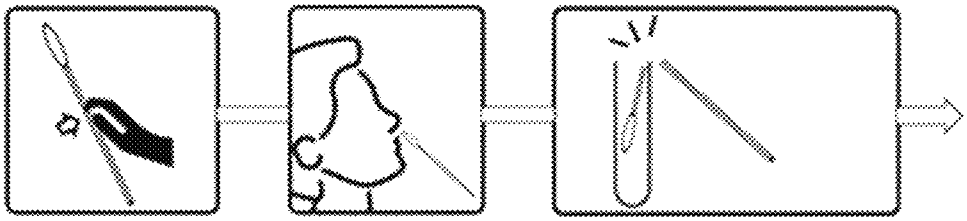
FIG. 8 illustrates a process of collecting nasal and oral swab specimens using the swab device for collecting a specimen of FIGS. 2 and 3, cutting the swab device in a break point, dipping the swab specimen in a specimen transport medium, and transporting the swab specimen to a testing site.
Figure 8:
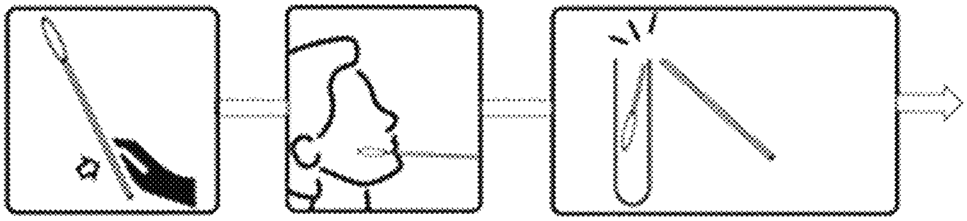
Figure 9:
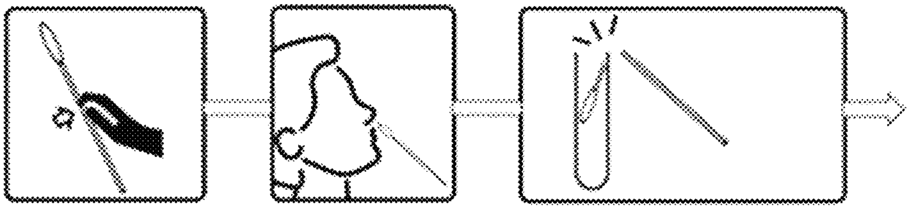
FIG. 9 illustrates a process of collecting a nasal and oral swab specimen using the swab device for collecting a specimen of FIG. 4, cutting the swab device in a break point, and dipping the swab specimen in a specimen transport medium to transport the swab specimen to a testing site. The nasal swab specimen collected using the swab device of FIG. 4 is cut in the first break point and then dipped in the specimen transport medium, and the oral swab specimen collected using the swab device of FIG. 4 is cut in the second break point and then dipped in the specimen transport medium.
Figure 9:
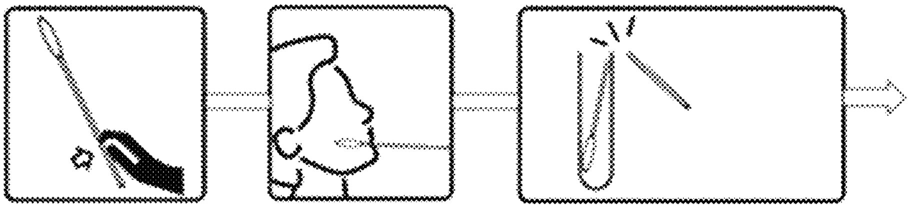
Figure 10:
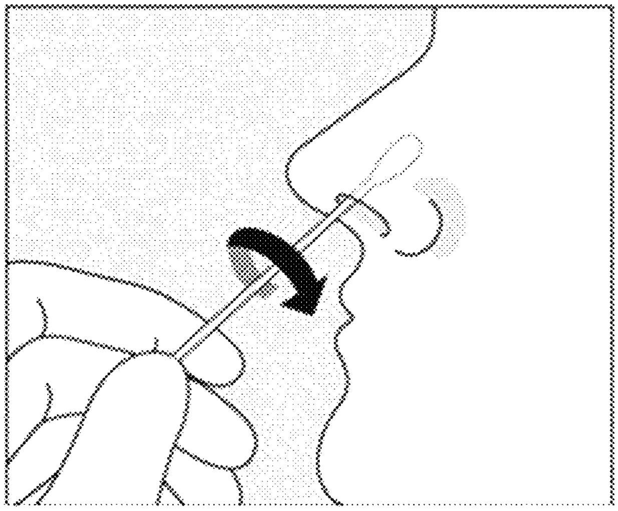
FIG. 10 shows an example of collecting a specimen from the nostril.
Figure 11:
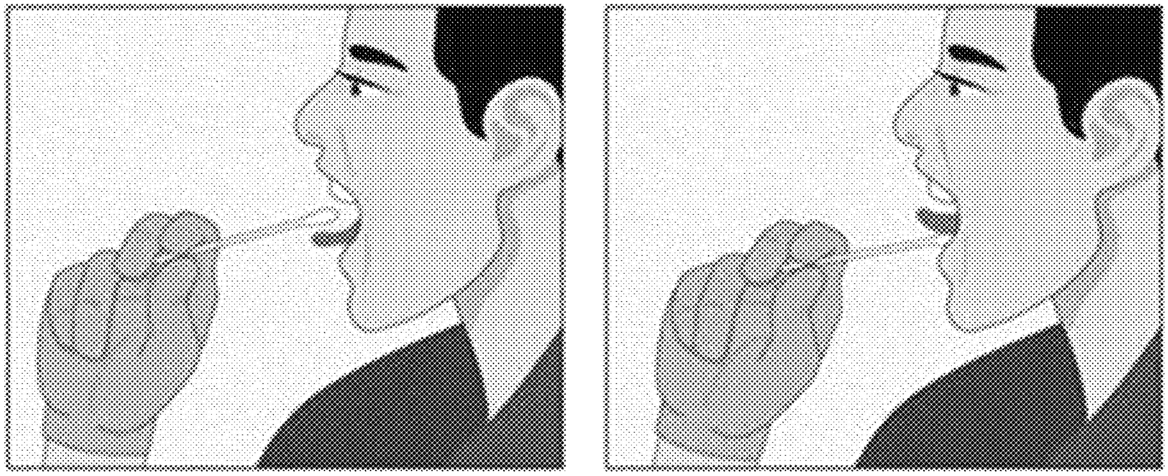
FIG. 11 shows an example of collecting a specimen from the oral cavity.

The swab device for collecting a specimen of FIG. 3 includes an elliptical (oval) head part having a fiber layer, and the thickness of the head part in a horizontal long axis portion is 5.0 mm and the thickness of the head part in a horizontal short axis portion is 3.0 mm. The fiber layer of the swab device is formed by coating polyester fiber of 3.30-3.35 Dtex with a flocking technique.

The first gripping point of the swab device was gripped, the swab device was inserted into the nostril by 2 cm, and swabbing was performed while gently rotating for 20 seconds, thereby obtaining a nostril swab specimen. After swabbing in one side of the nostril, swabbing in the other side of the nostril was performed. Then, the second gripping point of the swab device was gripped, and the swab device was applied to the sublingual portion to perform swabbing so that saliva was sufficiently absorbed by the fiber layer of the swab device, thereby obtaining an oral swab specimen.

Then, in a tube including a specimen transport medium, the swab device obtaining the nostril swab specimen was cut at the first break point, the swab device obtaining the oral swab specimen was cut at the second break point, and the nostril swab specimen and the oral swab specimen were immersed into CTM (Clinical Virus Transport Medium) (Noble Bio Company) or UTM (Copan Company) specimen transport medium, which are balanced salt solution-based buffer, together. Subsequently, a target nucleic acid to be added to the RT-PCR reactant was obtained by heat-treating the specimen transport medium or performing a nucleic acid separation process.

To obtain the target nucleic acid by heat treatment, the specimen transport medium in which the nostril swab specimen and the oral swab specimen were immersed was diluted to three times, and incubated at 98° C. for 3 minutes, thereby obtaining the target nucleic acid (hereinafter, referred to as "crude nucleic acid").

The nucleic acid isolation was carried out using the STARMag 96×4 Universal Cartridge Kit (Cat. No. 744300.4. UC384, Seegene Inc.) and the automatic nucleic acid extraction system, Microlab NIMBUS (Cat. No. 65415-02, Hamilton). The nucleic acid isolation was conducted according to the manual from the manufacturer of nucleic acid isolation reagents and the operation manual of the system. The nucleic acid isolation was conducted using 300 μl of the specimen transport medium in which the nostril swab specimen and the oral swab specimen were immersed (hereinafter, "isolated nucleic acid").

The RT-PCR reaction using the crude nucleic acid or isolated nucleic acid was performed using Allplex™ SARS-CoV-2 Assay (Seegene Inc.), which is a multiple one-step RT-PCR product. The Allplex™ SARS-CoV-2 Assay product is a one-step RT-PCR product for detecting a target gene (E gene) of both Sarbecovirus and SARS-CoV-2 and target genes (RdRP gene, S gene, and N gene) of SARS-CoV-2.

A reaction mixture of the RT-PCR reaction having a final volume of 20 μl was prepared using 5 μl of the crude nucleic acid or the isolated nucleic acid, 5 μl of enzymes (including chemically modified hot-start Taq polymerase, RTase, UDG, and RI), 5 μl of RNase-free Water, and 5 μl of SARS2 MOM (Oligo mix).

Each tube containing the prepared reaction mixture was placed in a real-time thermocycler (CFX96, Bio-Rad), and then reacted at 50° C. for 20 minutes, denatured at 95° C. for 15 minutes, followed by repeating 45 cycles of 10 seconds at 95° C., 15 seconds at 60° C., and 10 seconds at 72° C. The experiment was repeated twice to obtain an average Ct value.

As a result of the experiment, when the swab device for collecting a specimen of FIG. 3 was used, the positive rate of SARS-CoV-2 was equivalent to that of the swab device for collecting the nasopharyngeal and oropharyngeal specimens used in Comparative Example 1. Meanwhile, the swab device for collecting the nasopharyngeal and oropharyngeal specimens used in Comparative Example 1 took 3-4 times or more time to collect a specimen compared to the swab device for collecting a specimen of FIG. 3. In addition, in the case of using the swab device for collecting a specimen of FIG. 3, self-sampling by a general person who is a non-expert was also possible unlike the swab device used in Comparative Example 1.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A swab device for collecting a specimen, comprising:

(a) a head part having a fibrous layer formed to collect a specimen; and (b) a supporting part supporting the head part and having a break point formed on an outer surface; wherein the supporting part comprises a first gripping point and a second gripping point, and the first gripping point is located adjacent to the head part, and wherein the first gripping point and the second gripping point are each formed as an indication part indicating the gripping points, the indication part is a grippable shape and the grippable shape is a concave shape.

2. The swab device according to claim 1, wherein the supporting part is cut at the break point.

3. The swab device according to claim 1, wherein the length from the end of the head part to the first gripping point and the length from the end of the head part to the second gripping point have a ratio of 1:1.2-3.

4. The swab device according to claim 1, wherein the first gripping point is located between the head part and the break point, and the second gripping point is located between the break point and an end of the supporting part.

5. The swab device according to claim 4, wherein the length from the end of the head part to the first gripping point and the length from the end of the head part to the second gripping point have a ratio of 1:1.8-2.5.

6. The swab device according to claim 1, wherein the first gripping point and the second gripping point are located between the break point and the end of the supporting part.

7. The swab device according to claim 6, wherein the length from the end of the head part to the first gripping point and the length from the end of the head part to the second gripping point have a ratio of 1:1.2-1.8.

8. The swab device according to claim 1, wherein the break point of the supporting part is a first break point, the first break point is located between the head part and the first gripping point, the supporting part further comprises a second break point, and the second break point is located between the first gripping point and the second gripping point.

9. The swab device according to claim 8, wherein the length from the end of the head part to the first gripping point and the length from the end of the head part to the second gripping point have a ratio of 1:1.1-1.6.

10. The swab device according to claim 8, wherein the length from the end of the head part to the first break point and the length from the end of the head part to the second break point have a ratio of 1:1.8-2.5.

11. The swab device according to claim 1, wherein the overall length of the swab device is 140-180 mm.

12. A kit for collecting a specimen to detect a respiratory pathogen, comprising:

(a) the swab device for collecting a specimen of claim 1; and (b) a container comprising a specimen transport medium.

13. A method for collecting a specimen to detect a respiratory pathogen, comprising:

(a) obtaining a nasal swab specimen and an oral swab specimen by using the kit for collecting a specimen of claim 12; and (b) immersing the nasal swab specimen and the oral swab specimen in a specimen transport medium included in one container.

* * * * *